United States Patent [19]

Sharpe

[11] 4,398,089
[45] Aug. 9, 1983

[54] PENETRATION SENSING SYSTEM WITH RADIATION-EMITTING MATERIAL

[75] Inventor: James L. Sharpe, Morris Plains, N.J.

[73] Assignee: The United States of America as represented by the Secretary of the Army, Washington, D.C.

[21] Appl. No.: 217,408

[22] Filed: Jan. 4, 1972

[51] Int. Cl.³ .............................................. G01J 1/00
[52] U.S. Cl. .............................. 250/336.1; 250/506.1; 340/550; 340/571; 340/572
[58] Field of Search ............. 250/83.3 R, 106 R, 338, 250/339, 347, 372; 109/42 R; 252/301.1

[56] References Cited

U.S. PATENT DOCUMENTS

| | | | |
|---|---|---|---|
| 3,299,269 | 1/1967 | Hanson et al. | 252/301.1 X |
| 3,351,049 | 11/1967 | Lawrence | 252/301.1 X |
| 3,508,055 | 4/1970 | Wright et al. | 250/106 R |
| 3,654,464 | 4/1972 | Johnson et al. | 250/83.3 R |

Primary Examiner—Peter A. Nelson
Attorney, Agent, or Firm—Robert P. Gibson; Anthony T. Lane

[57] ABSTRACT

A system for protecting sealed or closed packaging means from tampering or unauthorized opening. A source of radiation cannot affect radiation sensors until the packaging means has been penetrated or tampered with. Then the radiation sensors set off a visual alarm, an audible alarm, or otherwise indicate that there has been an unauthorized penetration.

10 Claims, 5 Drawing Figures

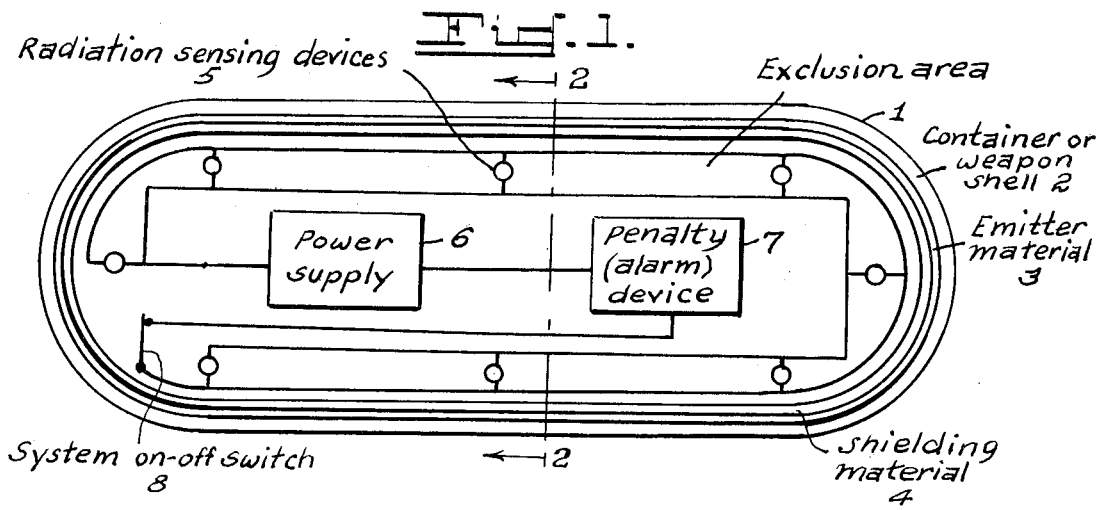
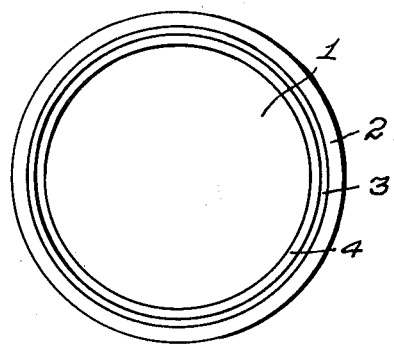

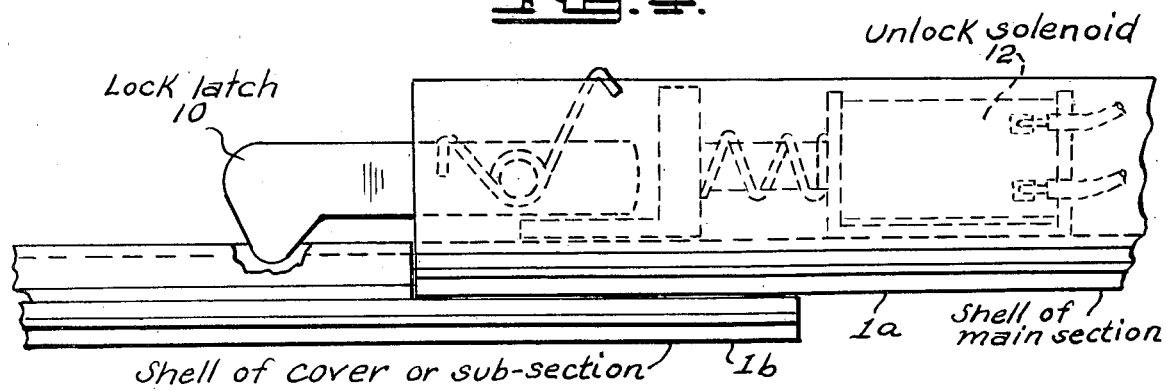
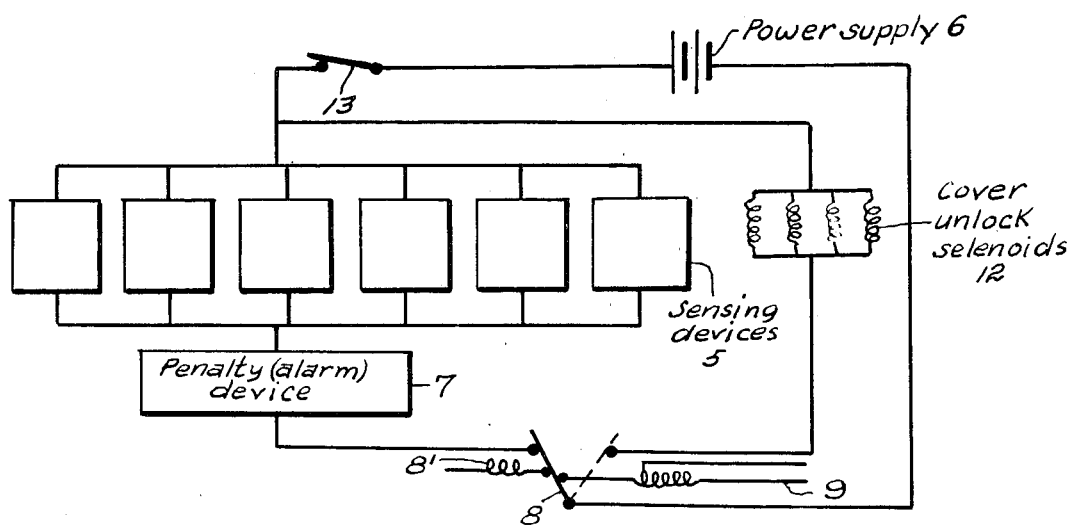

PENETRATION SENSING SYSTEM WITH RADIATION-EMITTING MATERIAL

The invention described herein may be manufactured, used and licensed by or for the Government for governmental purposes without the payment to me of any royalty thereon.

BRIEF SUMMARY

Weapons or other goods being shipped or stored in containers are sometimes subject to sabotage, tampering, pilfering, modification and so on. For large containers the problem of securing them against unauthorized penetration is difficult. Elaborate and expensive apparatus, security guards, and so on are in use.

The present invention discloses a system for detecting the penetration of a container. A source of radioactive material is used. That source is normally shielded. If the container is penetrated the radiation escapes and a sensor, or a plurality of sensors, detect the radiation. An alarm is triggered and appropriate steps may then be taken to abort the unauthorized opening and pilfering, tampering, sabotage, modification, or such.

IN THE DRAWING

FIG. 1 is a schematic illustration of a container embodying features of the invention;

FIG. 2 is a view along line 2—2 of FIG. 1;

FIG. 3 illustrates the signal transmission wire passing through a junction of container parts;

FIG. 4 illustrates a remote-controlled lock for a junction of container parts;

FIG. 5 schematically illustrates the basic electrical system.

A storage or shipping container 1 comprises an outer shell 2, a layer of radiation emitting material 3 and shielding material 4. Radiation sensing devices are connected to power supply 6 and penalty or alarm device 7 through on-off switch 8.

FIGS. 3 and 4 illustrate a junction of sections 1a and 1b of container 1. A flat wire cable, e.g., a code transmission line 9, passes through the overlapping sections. The overlapping sections include overlapping shielding material 4 as illustrated to avoid radiation leakage.

Two sections of the container may be secured together by spring-biased lock latch 10 and releasable by solenoid 12 as will be obvious to those skilled in the art.

The overall circuitry is illustrated in FIG. 5. Manual master-control switch 13 may be opened as desired to completely de-activate the system.

RADIATION SOURCE/SHIELD

Radiation emitting material 3 may be selected for alpha radiation or beta radiation, as two examples. If an alpha radiation emitter is used the shielding material 4 can be a very simple coating of plastic. However, the range of alpha particles in air is only about two inches or five centimeters. Therefore a large number of sensors would be needed for a large container, or a substantially continuous sheet-like sensor could be used.

If a beta radiation emitter is used at 3 the shielding material 4 can be a thin sheet of aluminum, or such. The range of beta particles in air is about sixteen feet or five meters. Therefore a small number of detectors would be sufficient.

OPERATION

Master control switch 13 is closed and container 1 is then assembled with overlapping sections 1a and 1b as illustrated in FIGS. 3 and 4. A coded signal is introduced to the apparatus through flat wire cable 9, or by other means as will be obvious to those skilled in the art. The coded signal allows switch 8 to move to the position illustrated in FIG. 5 under the influence of spring 8' to connect the power supply 6 in series with alarm device 7 and sensing devices 5. So long as there is no radiation from emitter 3 reaching a sensor 5 the circuit remains open and the alarm or penalty device 7 is not energized. However, if the container is penetrated the shielding material 4 will be punctured or otherwise ruptured and radiation from emitter 3 will be sensed by a sensor 5 thus completing the circuit to energize alarm or penalty device 7.

When it is desired to open the container a coded signal through cable 9 throws switch 8 to the dotted line position in FIG. 5. This disables the sensor/alarm system and energizes cover unlock solenoids 12 to release latches 10 thereby enabling the container sections to be separated.

I claim:

1. Apparatus for sensing penetration of a container, comprising radiation-emitting material substantially on all sides of said container, a radiation shielding rupturable member inside of said radiation-emitting material, and radiation sensing means inside of said radiation shielding member to sense radiation emissions or leakage if said radiation shielding member should be penetrated; said radiation shielding member completely shielding said radiation sensing means from radiation prior to rupturing of said radiation shielding member, so that only upon rupturing of said radiation shielding member the radiation emitted by said radiation-emitting material reaches said radiation-sensing means.

2. Apparatus as in claim 1 and an outer container outside of said radiation-emitting material.

3. Apparatus for sensing penetration of a container comprising radiation-emitting material substantially on all sides of the container, a radiation shielding member inside of said radiation-emitting material, radiation sensing means inside of said radiation shielding member to sense radiation emissions or leakage if said shielding member should be penetrated, means to activate said sensing means from a coded signal transmitted from outside of said container, and means to transmit such coded signal to said sensing means.

4. Apparatus as in claim 3 and locking means to lock sections of said container together, and means responsive to a coded signal to release said locking means.

5. Apparatus as in claim 1 and alarm or penalty means connected to said sensing means to indicate radiation emissions or leakage if said shielding member should be penetrated.

6. Apparatus as in claim 1 wherein said radiation emitting material emits alpha particles.

7. Apparatus as in claim 6 wherein said shielding member comprises a plastic film.

8. Apparatus as in claim 1 wherein said radiation emitting material emits beta particles.

9. Apparatus as in claim 8 wherein said shielding member comprises an aluminum film.

10. Apparatus as in claim 3 wherein said radiation shielding member is rupturable.

* * * * *